(12) United States Patent
Olivieri et al.

(10) Patent No.: US 6,995,209 B2
(45) Date of Patent: Feb. 7, 2006

(54) THERMALLY REVERSIBLE WATER IN OIL IN WATER EMULSIONS

(75) Inventors: Laetitia Olivieri, Paris (FR); Eyal S. Ron, Lexington, MA (US)

(73) Assignee: Madash LLC, Lexington, MA (US)

( * ) Notice: Subject to any disclaimer, the term of this patent is extended or adjusted under 35 U.S.C. 154(b) by 0 days.

(21) Appl. No.: 10/104,103

(22) Filed: Mar. 21, 2002

(65) Prior Publication Data

US 2003/0060559 A1  Mar. 27, 2003

(Under 37 CFR 1.47)

Related U.S. Application Data (60) Provisional application No. 60/277,666, filed on Mar. 21, 2001.

(51) Int. Cl.
*C08L 71/00* (2006.01)
*C08L 101/12* (2006.01)
*A61K 31/00* (2006.01)

(52) U.S. Cl. .................. 524/801; 428/913; 514/938; 514/939; 514/941; 525/90

(58) Field of Classification Search ............... 428/913; 514/938, 939, 941, 1; 524/801; 525/90
See application file for complete search history.

(56) References Cited

U.S. PATENT DOCUMENTS

| | | | |
|---|---|---|---|
| 4,474,752 A | | 10/1984 | Haslam et al. |
| 5,252,318 A | | 10/1993 | Joshi et al. |
| 5,292,516 A | | 3/1994 | Viegas et al. |
| 5,548,035 A | | 8/1996 | Kim et al. |
| 5,599,534 A | | 2/1997 | Himmelstein et al. |
| 5,622,649 A | * | 4/1997 | Hunter et al. .............. 516/29 |
| 5,702,717 A | | 12/1997 | Cha et al. |
| 5,750,124 A | * | 5/1998 | Gohla et al. .............. 424/401 |
| 5,939,485 A | | 8/1999 | Bromberg et al. |
| 6,004,573 A | | 12/1999 | Rathi et al. |
| 6,316,011 B1 | * | 11/2001 | Ron et al. .................. 424/401 |

FOREIGN PATENT DOCUMENTS

| | | |
|---|---|---|
| EP | 0 583 814 A1 | 2/1994 |
| JP | 07-018042 A2 | 1/1995 |
| WO | WO 95/24430 A2 | 9/1995 |
| WO | WO 97/00275 A2 | 1/1997 |

OTHER PUBLICATIONS

Schultz et al., Macromolecular Complexes in Chemistry and Biology, Eds. Dubin/Bock/Davis/Theis Springer–Verlag Berlin Heidelberg, pp. 1–13 (1994).
V. Muguet et al., Journal of Colloid and Interface Science, vol. 218, 335–337 (1999).
I. Terrisse et al., Colloids and Sirfaces A: Physiochemical and Engineering Aspects vol. 91, 121–128 (1994).
V. Muguet et al., Journal of Rheology vol. 44, No. 2, 379–396 (Mar.–Apr. 2000).
N. Jager–Lezer et al., Journel of Controlled Release vol. 45, 1–13 (1997).
L. Bromberg and E. Magner, Langmuir vol. 15, 6792–6798 (Sep. 1999).
L.E. Bromberg and E.S. Ron, Advanced Drug Delivery Reviews vol. 31, 197–221 (1998).
P.D. Huibers et al., Macromolecules vol. 32, 4889–4894 (Jun. 1999).
L. Bromberg, Macromolecules vol. 31, 6148–6156 (Sep. 1998).
L.E. Bromberg and D.P. Barr, Macromolecules vol. 32, 3649–3657 (Apr. 1999).
Lev Bromberg, Langmuir vol. 14, 5806–5812 (Sep. 1998).
L. Bromberg et al., Langmuir vol. 16, 2609–2614 (Jan. 2000).
L. Bromberg and Marina Temchenko, Langmuir vol. 15, 8627–8632 (Sep. 1999).
L. Bromberg and E. Magner Langmuir vol. 15, 6792–6798 (Sep. 1999).
Lev Bromberg, Ind. Eng. Chem. Res. vol. 37, 4267–4274 (Sep. 1998).
www.ff.ukim.edu.mk/pro–multi.htm (Mar. 21, 2002).

* cited by examiner

*Primary Examiner*—Kelechi C. Egwim (57) ABSTRACT

A thermally reversible water in oil in water (W/O/W) emulsion including a thermally reversible viscosifying polymer in the continuous aqueous phase of the emulsion. The thermally reversible viscosifying polymer of the W/O/W emulsion includes a block copolymer having at least a first polyoxyalkylene block having a hydrophobic region and a hydrophilic region effective to form micelles in solution in response to a change in temperature, and at least a second block comprising a poly(vinylcarboxylic acid).

28 Claims, 5 Drawing Sheets

THERMALLY REVERSIBLE WATER IN OIL IN WATER EMULSIONS

RELATED APPLICATIONS

This application claims priority under 35 U.S.C. § 119(3) to co-pending provisional application serial No. 60/277,666, filed Mar. 21, 2001 entitled "Thermally Reversible Water/Oil/Water Emulsion."

BACKGROUND OF THE INVENTION

Emulsion are a mixture of two or more immiscible liquids: One liquid forms a continuous phase in which the other liquid is dispersed in the form of small drops. Commonly, the continuous phase is water or another polar solvent and the dispersed phase is an oil. However, other possibilities exist including inverted emulsions (water dispersed in oil) and double emulsions (water in oil in water). Water-in-oil-in-water (W/O/W) double emulsions are vesicular systems composed of small aqueous droplets contained in larger oily droplets which, in turn, are dispersed in a continuous aqueous phase. The applications of these systems range from pharmaceutical drug delivery to foods and cosmetics. Some benefits of these emulsions include the protection of the entrapped substances, their capacity to incorporate several actives in the different emulsion compartments, and their sustained release effect.

Two important release mechanisms are often cited in the literature: i) the diffusion of the active agent through the oily barrier; and ii) the droplets bursting that occurs either by dilution in a hypo-osmotic solution (with regards to the internal aqueous phase) or by submission to a shear stress.

Deformation under shear and the bursting of simple, dilute emulsions has been investigated. The break up occurs when shear stress exceeds cohesion stress, which is defined as a capillary number $Ca=\eta_c Gr/\sigma$, where $\eta_c$ is the continuous phase viscosity, G the shear rate, r the radius of the globule at rest and $\sigma$ the interfacial tension between oil and water. Bursting occurs when this capillary number exceeds a critical value $Ca_{cr}$ close to unity. This relation points out that the thickening of the continuous phase is an important factor to encourage the globules bursting.

Thus, thickening of the external aqueous phase of water-in-oil-in-water (W/O/W) multiple emulsions is desired to increase the release under shear during use. However, it leads to the micelles bursting during fabrication because the additional viscosity causes the emulsified droplets to rupture under ordinary fabrication conditions.

SUMMARY OF THE INVENTION

The present invention is directed to W/O/W emulsions containing a thermo-responsive hydrogel in the continuous aqueous phase. A thermoviscosifying hydrogel or polymer undergoes large changes in viscosity with a small change in temperature. The thermally responsive hydrogel creates stable double emulsions that gel, i.e., thicken or viscosify, at skin temperature (30–35 C.), but that do not gel under fabrication or storage conditions at room temperature. The shear-sensitive W/O/W multiple emulsion of the invention experiences break up of the droplets (and thus the release of an active ingredient) upon shear above the viscosification temperature (where the emulsion is of high viscosity and experiences high shear stress), but not during the fabrication process at room temperatures or below (where the emulsion is of low viscosity and experiences low shear stress). Agents entrapped in the emulsion droplets are released at body temperature after a topical application.

One aspect of the invention provides a thermally reversible water in oil in water (W/O/W) emulsion having a continuous aqueous phase that includes a thermally reversible viscosifying polymer.

In at least some embodiments, the thermally reversible viscosifying polymer includes a block copolymer comprising at least a first polyoxyalkylene block having a hydrophobic region and a hydrophilic region effective to form micelles in solution in response to a change in temperature, and at least a second block comprising a poly(vinylcarboxylic acid).

In at least some embodiments, the block copolymer is a linear block copolymer. In at least some embodiments, the block copolymer is a random block copolymer.

In at least some embodiments, the polyoxyalkylene includes polyoxyethylene as the hydrophilic region and polyoxypropylene as the hydrophobic region. In at least some embodiments, the polyoxyalkylene comprises a triblock polymer of polyoxyethylene (POE) and polyoxypropylene (POP) having the formula $(POE)_a(POP)_b(POE)_a$, where a is in the range of 100–50, and b is in the range of 50–70. In at least some embodiments, the polyoxyalkylene contains between 70 and 90 wt % polyoxyethylene, or it contains a range from 10–80 wt % polyoxyethylene. In at least some embodiments, the molecular weight of the polyoxypropylene is between: 950 and 4000, or in at least some embodiments between 2000–4000.

In at least some embodiments, the poly(vinylcarboxylic acid) is selected from the group consisting of acrylic acid, substituted acrylic acids, methacrylic acid, substituted methacrylic acids, and ionized forms thereof.

In at least some embodiments, the viscosification occurs at a temperature in the range of about 30 to 37° C.

In at least some embodiments, the thermally reversible viscosifying polymer comprises about 0.01 to 20 wt % of the continuous aqueous phase, or the thermally reversible viscosifying polymer comprises about 0.1 to 10 wt % of the continuous aqueous phase, or the thermally reversible viscosifying polymer comprises about 0.01 to 1 wt % of the continuous aqueous phase.

In at least some embodiments, active agents are entrapped within the discontinuous water phase or in the discontinuous oil phase droplets of the W/O/W emulsion.

In another aspect of the invention, a method of reducing shear sensitivity in a water in oil in water (W/O/W) emulsion includes introducing a thermally reversible viscosifying polymer into the continuous aqueous phase of the W/O/W emulsion.

In another aspect of the invention, a pharmaceutical composition includes a water in oil in water emulsion having a continuous aqueous phase, wherein the continuous aqueous phase comprises a thermally reversible viscosifying polymer; and at least one active agent in the oil or water discontinuous phase.

The W/O/W double emulsion of the invention provides an easy fabrication process with a higher entrapment yield, and a higher fraction release of encapsulated materials at 35° C. compared with other double emulsions.

By "gelation" or "viscosification" as those terms are used herein, it is meant an increase in the viscosity of the polymer solution. Gelation is dependent on the initial viscosity of the solution, but typically a viscosity increase at pH 7 and 1 wt % polymer concentration is in the range of about 2- to 100-fold, or about 5- to 50-fold, or about 10- to 20-fold for an aqueous phase used in the preparation of W/O/W emulsions of the invention. The extent of viscosification is determined relative to a simple polymer solution (without emulsion droplets) and the effect may be modified somewhat in the final emulsion.

By "reversibly gelling" or "reversibly viscosifying," as those terms are used herein, it is meant that the process of gelation takes place upon an increase in temperature rather than a decrease in temperature. This is counter-intuitive, since solution viscosity typically decreases with an increase in temperature.

By "end-modified," as that term is used herein, it is meant that the polyoxyalkylene component is modified at its termini by chemical conversion and/or addition to the component. This in contrast to modifications which may occur along the backbone of a polymer resulting in a random or crosslinked block copolymer.

As used herein the term "about" refers to ±10% of the stated value.

BRIEF DESCRIPTION OF THE DRAWING

Various objects, features, and advantages of the present invention can be more fully appreciated with reference to the following detailed description of the invention when considered in connection with the following drawing, in which like reference numerals identify like elements. The following drawings are for the purpose of illustration only and are not intended to be limiting of the invention, the scope of which is set forth in the claims that follow.

DETAILED DESCRIPTION OF THE INVENTION

According to at least some embodiments of the invention, a thermally reversible viscosifying W/O/W emulsion includes a thermally reversible viscosifying polymer in the continuous aqueous phase. In at least some embodiments, the thermally reversible viscosifying polymer is a block copolymer of poly(vinylcarboxylic acid) component and a polyoxyalkylene component. The copolymer can be a linear block copolymer, a random block copolymer, a branching block copolymer or an end modified block copolymer.

The polyoxyalkylene component contains a hydrophilic region and a hydrophobic region which makes it able to change its degree of association and/or agglomeration in response to an environmental stimulus. The stimulus most commonly is temperature, pH, ionic concentration, or solvent concentration, but other stimuli are within the scope of the invention if they cause the polyoxyalkylene to aggregate. Temperature is a preferred environmental trigger. The aggregation may be in the form of micelle formation, precipitation, labile crosslinking or other factors.

In at least some embodiments, the polyoxyalkylene component can itself be a thermogelling polymer, such as Pluronics® (BASF, Ludwigshafen, Germany). Exemplary polyoxyalkylenes are block copolymers of polyoxyethylene and polyoxypropylene having the general formula of a triad ABA block copolymer, $(POE)_a(POP)_b(POE)_a$, where POE= ethylene oxide and POP=propylene oxide moieties. Pluronic® (BASF) triblock polymers are commercially available for a in the range of 6 to 140 and b ranging from 6–100. In at least some embodiments the Pluronic® (BASF) triblock polymers has a in the range of 50–100 and b ranging from 50–70. In at least some embodiments, the polyoxyalkylene contains between 70 and 90 wt % polyoxyethylene, or it contains a range from 10–80 wt % polyoxyethylene. In at least some embodiments, the molecular weight of the polyoxypropylene is between: 950 and 4000, or in at least some embodiments between 2000–4000.

Other exemplary polyoxyalkylene polymers include alkyl poloxamers, which are a product of alcohol condensation reactions with a terminal alkyl or arylalkyl group. The alkyl group should have hydrophobic character, such as butyl, hexyl and the like. An alkyl poloxamer may have the general formula R—$(OCH_2CH)_n$OH, where R is a nonpolar pendant group such as alkyl and arylalkyl and the like, and n is in the range of 5–1000. A preferred alkylpoloxamer is polyethyleneglycol mono(nonylphenyl)ether.

One or more polyoxyalkylene components may be used in the reversibly gelling composition of the present invention.

In at least some embodiments of the invention, the poly (vinylcarboxylic acid) component includes linear, branched and/or crosslinked polymers. Of particular interest are vinylcarboxylic polymers of monomers such as acrylic acid, methacrylic acid, ethacrylic acid, phenyl acrylic acid, pentenoic acid and the like. In at least some embodiments, the carboxyvinyl polymer includes poly(acrylic acid) and its salts. One or more poly(carboxyvinyl) polymers may be used in the thermally reversible viscosifying polymers of the present invention. Copolymers, such as by way of example only, copolymers of acrylic acid and methacrylic acid, are also contemplated. In at least some embodiments, the poly (carboxyvinyl) polymer or oligomer is ionized, and in particular is ionized poly(acrylic acid). Ionized poly(acrylic acid) (PAA) is bioadhesive or mucoadhesive (adheres well to mucosal and dermal surfaces), which is advantageous for topical applications.

In at least some embodiments of the invention, the thermally reversible viscosifying block copolymer includes a polyoxyalkylene component capped by both ends by oligomer of a carboxyvinyl component, referred to herein as an "end-modified block copolymer." The end-modified polyoxyalkylene compositions of the invention exhibit a reversible gelation at body temperature (25–40° C.) and/or at physiological pH (ca. pH 3.0–9.0) and even in basic environments up to pH 13 (e.g., the gastro-intestinal environment) are particularly preferred for pharmaceutic and personal care applications.

End-modified polyoxyalkylene block copolymer solutions at appropriate pH exhibit flow properties of a liquid at about room temperature, yet rapidly thicken into a gel consistency of at least about five times greater, preferably at least about 10 times greater, and even more preferably at least about 30 times and up to 100 times greater, viscosity upon increase in temperature of about 10° C. and preferably about 5° C. The reversibly gelling composition of the present invention exhibit gelation even at very low polymer concentrations. Further information on end-modified polyoxyalkylene polymers is found in U.S. Pat. No. 6,316,011, herein incorporated by reference.

The novel interaction between the constituent polymers components of the reversibly gelling composition permits formation of gels at very low solids content. Gelation and/or viscosification is observed in aqueous solutions having about 0.01 to 20 wt % of the polyoxyalkylene component and about 0.01 to 20 wt % of the end-modifying polymer component. A typical reversibly gelling composition may be comprised of about 0.01 wt % to about 1 to 8 wt %, preferably less than about 4 wt % of total polymer solids (e.g., polyoxyalkylene and biocompatible polymer), and more preferably less than 1 wt % total polymer solids, while still exhibiting reverse thermal viscosification. Of course, the total solids content of the composition, including additives and the pharmaceutic agent, may be much higher.

The relative proportion of polyoxyalkylene polymer and end-modifying polymer may vary in the composition, dependent upon the desired properties of the composition. A 1:3 to 3:1 mixture of polyoxyalkylene and poly(acrylic acid), or a 1:1 mixture of polyoxyalkylene and poly(acrylic acid), provides the desired thermoviscosifying effect under most circumstances.

The end-modified polyoxyalkylene polymer is incorporated into the continuous aqueous phase of a W/O/W emulsion and can function as a temperature sensitive thickening agent, and in addition possesses surfactant and emulsifying capabilities which may be beneficial in a pharmaceutic or personal care composition. The reversibly gelling composition imparts thickening properties to the emulsion at the use and/or application temperature. Such thickening properties include enhanced overall viscosity, as well as a desirable viscosity response with temperature.

In at least some embodiments, the thermally reversible viscosifying polymer includes hydrophobically modified poly(vinylcarboxylic acid) having poly(propylene oxide) (PPO) block as a hydrophobic component contained within a polyoxyalkylene block. Suitable polyoxyalkylene block polymers and poly(vinylcarboxylic)acid polymers are those described herein above. In at least some embodiments, the hydrophobically modified poly(acrylic acid) includes a random copolymer of poly(acrylic acid) and triblock polyoxyalkylene copolymers. The random copolymer includes Suitable random copolymers of poly(acrylic acid) and triblock copolymers are described in U.S. Pat. No. 5,939,485, which is incorporated herein by reference These hydrophobically modified poly(acrylic acid) copolymers are capable of stabilising emulsions and forming thermoreversible shear thinning hydrogels at body temperature. This occurs without phase separation, at low polymer concentrations (1–5 wt %) and with a rapid $10^3$–$10^4$ fold increase in viscosity over a range of several degrees, when neither sub-components (poly(acrylic acid) or polyoxyalkylene) shows any sign of viscosification.

A general method of making the random copolymer of poly(acrylic acid) and triblock polyoxyalkylene polymer includes solubilization of the polyoxyalkylene in acrylic acid monomer. The monomer is polymerised to form poly(acrylic acid), during which time the polyoxyalkylene block is incorporated into the growing chain, either as a component of the backbone, or as a crosslinking component. Polymerisation is accomplished by addition of a polymerisation initiator or by irradiation techniques. The initiator may be a free radical initiator, such as chemical free radical initiators and UV or gamma radiation initiators. The resultant random copolymer exhibits thermally reversible viscosification at low solids contents and in the room temperature to body temperature regime. Performance is somewhat variable due to the poor control over polymerisation conditions during formation.

The reversibly gelling polymers described above is used to form a water in oil in water emulsion using conventional methods. Most emulsions are formed by ripping droplets apart with shear forces (usually by stirring) or inertial forces (usually by impact). There are a number of techniques to make emulsions. Depletion force fractionation relies on the fact that for identical materials large objects rise faster than small objects (the buoyancy force is proportional to the volume while the drag force goes like the drop diameter). To fractionate a poly-disperse emulsion, additional particles are added to the continuous phase. These particles constantly bang into the emulsion drops and if the emulsion drops are sufficiently large, produce an effective attractive force between emulsion drops. Then, these larger drops cluster together and rise relatively quickly to the top of the emulsion while the smaller emulsion drops remain suspended. Continued modification of the size and density of the depletion particles is then used to size segregate the emulsion.

Because of surface tension, a cylinder of fluid is unstable and will break up into drops. To make a fluid cylinder, liquid is forced through a nozzle or other small opening at a relatively high speed which forms a jet. In order to form an emulsion, the drops are added to a continuous phase.

A drop hanging from the end of a tube is held up by interfacial tension and pulled down by gravity. If fluid is being added to the drop, a point will be reached where the gravitational force exceeds the interfacial force and the drop is pulled away from the tube. By placing the tube in an axially flowing fluid, the drop will feel a drag force proportional to the drop size and, again, when this force is large enough the drop will break away from the tube.

Multiple W/O/W emulsions are suitable vehicles for providing a modified drug release rate. Drug release rate could be varied by osmotic effect of incorporated ingredients. In the case of redispersed W/O/W emulsions obtained from the phase inverted W/O emulsion, drug release rate could be modified by changing the redispersion conditions—volume ratio of dispersed phase and concentration of hydrophilic surfactant in redispersing medium.

The invention is described with reference to the following examples, which are presented for the purpose of illustration only and is not intended to be limiting of the invention.

EXAMPLE 1

The example describes the synthesis of poloxyalkylene:poly(acrylic acid) block copolymer.

A poloxamer was derivatized to obtain an acryloyl-terminated poloxamer according to the following equation.

$$HO\text{—}EO_{100}PPO_{65}EO_{100}\text{—}OH. + H_2CCHC(O)Cl + amine. \rightarrow$$
$$CH_2\text{=}CHO(O)\text{—}EO_{100}PPO_{65}EO_{100}\text{-}OOCH\text{=}CH_2 + HCl \quad (1)$$

Pluronic F127 ($EO_{100}PPO_{65}EO_{100}$; 30 g; BASF, Germany) was dissolved in dry toluene in a 250 mL round bottomed flask equipped with a magnetic stirrer and gas inlet-outlet to which 2.1 g triethylamine (Aldrich, 99+%) was added dropwise while stirring at 50° C. under nitrogen blanket. Then 1.2 mL of acryloyl chloride (Aldrich, 96%) was added dropwise into the flask. followed by addition of 0.75 mL triethylamine in 5 mL toluene under constant flow of nitrogen. The reaction mixture was stirred at 50° C. for 1.5 h and the contents were cooled to ambient temperature and filtered. All liquids were evaporated under vacuum and the resulting polymer flakes were redissolved in 200 mL toluene and precipitated by addition of hexane. The steps of dissolution and precipitation ere repeated, and the polymer was finally dissolved in a minimum amount of methylene chloride and washed with excess hexane in a separation funnel. The polymer was then dried under vacuum ($10^{-3}$ Torr) at 20° C.

The acryloyl-modified poloxamer was then end-linked with poly(acrylic acid) by free radical polymerization according to eq (2).

ronic® F108 and poly(acrylic acid). This example also characterises the gelation and the physical properties of the resultant thermally reversible viscosifying polymer in solution.

Block copolymer of propylene oxide (POP) and ethylene oxide (POE) having sandwich structure $(POE)_a(POP)_b(POE)_a$ (Pluronic F108 NF, Poloxamer 338 NF, where "F" means Flakes, "10" means 10.×300=3000—MW of the polypropylene oxide) section of the block copolymer, "8" means that the weight percentage of ethylene oxide in the copolymer is 80%, and nominal molecular weight is 14,600, 3.0 g) was dissolved in 3.0 g acrylic acid (Aldrich). The solution was deaerated by $N_2$ bubbling for 0.5 h and following addition of 100 μl of freshly prepared saturated solution of ammonium persulfate Kodak) in deionized water was kept at 70° C. for 16 h resulting in a transparent polymer.

A known amount of the resultant polymer was suspended in 100 ml deionized water into which NaOH was added.

Acrylic acid (30 g Aldrich, 99%) was neutralized by addition of 50 wt % aqueous NaOH solution while stirring. The degree of neutralization of acrylic acid was 6 mol %. Upon redissolution of precipitate, acryloyl-terminated poloxamer was charged into a flask and allowed to completely dissolve in acrylic acid under constant agitation. A 500 mL multinecked thermostated flanged glass reactor equipped with a mechanical stirrer, syringe sampler, thermometer, programmable heater bath and a gas inlet/outlet was charged with 400 mL of poly(vinyl alcohol) (99% hydrolyzed, MW 13,000, Aldrich) solution in dodecane and was deoxygenated overnight by nitrogen flow while stirring. A freshly prepared initiator system comprising 5 mL of freshly prepared ammonium persulfate (Aldrich, 99.9+%; 300 mg) and N,N,N',N'-tetramethylethylenediamine (Aldrich, 99.5%; 0.1 mL) in water/acrylic acid mixture was added into the solution of poloxamer in acrylic acid while stirring. The resulting solution was immediately introduced into the reactor under nitrogen blanket while stirring. The reactor was allowed to equilibrate at ambient temperature, the nitrogen flow was discontinued and the slurry of the resulting polymer was filtered off using Whatman filter paper (retention 10 μm). The polymer was repeatedly washed with excess heptane and then with excess hexane in a separation funnel. The resultant white powder was dried under vacuum at 40° C. for 24 h.

EXAMPLE 2

This example describes the synthesis of a random copolymer thermally responsive viscosifying polymer using Plu- Following swelling for 3 days while stirring, the pH of the resulting fine suspension was adjusted to 7. The polymer was viscosified (liquid to gel transition on raising the temperature from room temperature) at temperatures of around 34° C. and higher at pH 7. Repeated heating and cooling of the polymer solution did not degrade the gelling effect.

EXAMPLE 3

This example describes the preparation of a W/O/W emulsion of the invention and compares its performance against an emulsion containing a thickener (poly(acrylic acid)) that does not markedly change its viscosity properties with temperature.

Preparation of the Multiple Emulsions

The composition (wt %) of multiple emulsions is given in Table I, where EMP Hydrogel™ refers to the end-modified polyoxyalkylene block copolymers described herein above and Carbopol® is an acrylic acid copolymer available under the registered trademark from Noveon Inc.

The oil was an isohexadecane (Arlamol® HD, ICI, France). A polymeric lipophilic surfactant, a PEG-30 dipolyhydroxystearate with A-B-A structure (Arlacel® P135, ICI, France), was used to emulsify the W/O primary emulsion. Since the formulation of the W/O/W multiple emulsion required a hydrophilic surfactant, an ethylene and propylene oxide copolymer (Arlatone® F127G, ICI, France) was chosen, which is non-ionic. The surfactant concentrations were chosen in order that the interfaces were saturated based on respective critical Micelle conentration (CMC) values of the two surfactants. The sodium chloride (NaCl) was purchased from Prolabo (France) and used in order to increase the stability of the system and to play the role of a breakdown indicator. Poly(ethylene oxide)-b-poly(propylene oxide)-b-poly(ethylene oxide)-g-poly(acrylic acid) copolymer (EMP Hydrogel™) is a copolymer of Pluronic® F127 and poly(acrylic acid) (average molecular weight $3 \times 10^6$ Da) obtained via modification of the Pluronic® at both ends by acryloyl moieties following copolymerization. We used an EMP Hydrogel™ concentration that allowed a $10^3$–$10^4$ fold increase in viscosity over a range of 20 to 40° C. Lightly cross-linked PAA (Carbopol® 974-P, B. F. Goodrich, France) was applied to prepare a reference emulsion. The concentration of this component was chosen in order to have an equivalent viscosity to the EMP Hydrogel™ multiple emulsion at room temperature.

|  | Multiple emulsion thickened by EMP Hydrogel | Multiple emulsion thickened by Carbopol ® 974-P | Multiple emulsion thickened by Carbopol ® 974-P |
|---|---|---|---|
| W/O primary emulsion |  |  |  |
| Demineralised water | 66.7 | 66.7 | 66.7 |
| NaCl | 0.3 | 0.3 | 0.3 |
| Arlamol ® HD | 29 | 29 | 29 |
| Arlacel ® P135 | 4 | 4 | — |
| Abil ® EM90 | — | — | 4 |
| W/O/W multiple emulsion |  |  |  |
| W/O primary emulsion | 60 | 60 | 60 |
| Demineralised water | 36.8 | 37.2 | 37.2 |
| Arlatone ® F127G | 1.6 | 1.6 | 1.6 |
| EMP Hydrogel ™ | 1.6 | — | — |
| Carbopol ® 974-P | — | 0.4 | 0.4 |
| 10% NaOH solution | — | 0.8 | 0.8 |

Multiple emulsions named respectively EMPME (multiple emulsion thickened by EMP Hydrogel™) and CME (multiple emulsion thickened by Carbopol® 974-P) were prepared with a Rayneri mixer by, respectively, a two or three step process. The W/O primary emulsions were obtained by incorporation of the aqueous phase into the oily phase containing the lipophilic surfactant, after heating the two phases to 70–80° C., under high stirring (3000 rpm) for 45 minutes. The resulting W/O primary emulsions were dispersed gradually into the aqueous phase containing the hydrophilic surfactant and the polymer (EMP hydrogel™ or Carbopol® 974-P) under moderate stirring (500 rpm) for 15 minutes, at 15° C. The resulting pH of EMPME was around 6. The formation of the multiple emulsion gelled with the carboxyvinylic polymer required a third step which was the carbomer neutralization by a 10% sodium hydroxide solution to obtain a pH around 6 (skin pH). A third W/O/W multiple emulsion was also prepared using another lipophilic surfactant, a cetyl dimethicone copolyol (Abil® EM90, Goldschmidt, France), to assess the role of the lipophilic surfactant in the release mechanisms.

Firstly, thermogelling properties of 4 wt % EMP Hydrogel™ solution and corresponding multiple emulsion were studied with a controlled stress rheometer (CSL 100, Carrimed, France) using a cone and plate geometry which allows a homogeneous shear of the samples (plate, 40 mm; cone, 2°). Samples (volume 0.1 ml) were tested under constant stress of 10 Pa in the range of temperatures from 20 to 40° C.

Secondly, the multiple emulsions behaviour under shear was studied by different methods including rheology, granulometry, conductometry and microscopy. All measurements were performed 24 hours after preparation.

To simulate a topical application, multiple emulsions were sheared for 3 minutes at different shear stresses with a controlled stress rheometer (RS 100, Carrimed, France) at 20, ml).

The granulometric analysis was carried out with a laser diffraction granulometer (Coulter LS 230, Coultronics, France), equipped with a "microvolume" cell of 12 ml designed for liquid samples, to study the multiple globules fragmentation under shear. Each sample was diluted (dilution factor of $10^4$–$10^5$) in order to obtain the convenient optical concentration, between 8 and 12%, to achieve the measure in optimal conditions. An iso-osmotic glucose solution with regard to the internal aqueous phase was used for the dilution to prevent globules from bursting; as the internal aqueous phase was a little hyper-osmotic with regard to water, a dilution in pure water (which is hypo-osmotic) would provoke an osmotic water flow from the external to the internal phase which would lead to the swelling and then the breakdown of the globules. The globule size distributions, characterized thanks to the Fraunhoffer model, were given as a function of the volume and the diameter of the globules. The defined diameter was the mean diameter "volume-moment" $d_{32}$ (chosen as it took specially the big globules into account; these ones, including the major part of the internal aqueous phase, were of great interest in this study):

$$d_{32} = \frac{\sum n_i d_i^3}{\sum n_j d_j^2}$$

where $n_i$ is the number of the particles having a $d_i$ diameter.

Changes in the droplet size as a function of the shear rate in multiple emulsions were also monitored before and after shearing with an optical microscope (Olympus BX60, Olympus, France) connected to a video camera (Sony, France).

To evaluate the entrapment yield, conductivity of each multiple emulsion diluted (1/20) in the iso-osmotic glucose solution was measured during the storage time with a CDM 230 conductometer (Tacussel, Radiometer Copenhagen, France). Based on the estimate of the NaCl amount in the external aqueous phase, entrapment yields can be calculated using the corresponding calibration curve. These calibration curves were expressed in conductivity ($\mu$S/cm) as a function of NaCl concentration (mg/ml). The equation of the calibration curve was $$y = 1679.1x + 5.10^{-5} (R^2 = 0.99)$$

The thermo-gelling properties of the for the most stable W/O/W multiple emulsions were assessed between 20 and 40° C. and the fraction released under shear at 20° C. and 35° C.

As the shear rate values are better defined than the shear stress when skin application is concerned, the break up and release curves are given as a function of the shear rate which values are arbitrarily taken at the beginning of each 3 minutes stress ramp.

Figure 1:
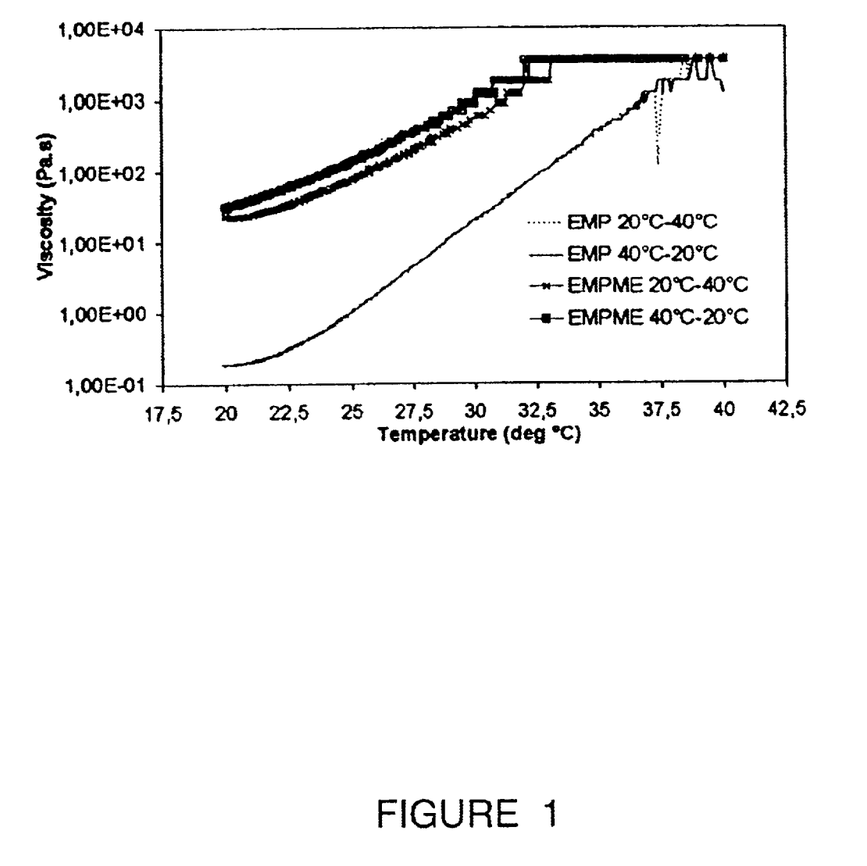
FIG. 1 is a thermal viscosification measurement in the range of 20 to 40° C., for a poly(acrylic acid) (PAA) end-modified polyoxyalkylene polymer (4 wt %) and the corresponding multiple emulsion (EMPME) at 10 Pa shear stress.

Thermal Viscosification Measurement for EMP Hydrogel™ and the Corresponding Multiple Emulsion EMPME Thermoviscosifying behaviours of EMP Hydrogel™ in solution and in multiple emulsion are illustrated in FIG. 1.

As is seen, a $10^4$-fold increase in hydrogel viscosity (equilibrium viscosity) occurred over a range of temperatures from 22° C. to 37.5° C. The Hydrogel multiple emulsion also gelled with increasing temperatures, but to a lower extent, which was probably due to the dilution factor of the thermogelling copolymer solution in the multiple emulsion but also to the use of additional emulsion additives which could indeed interfere with the gelation process. The sol-gel transition of both the EMP Hydrogel™ and the multiple emulsion had no hysteresis.

Figure 2:
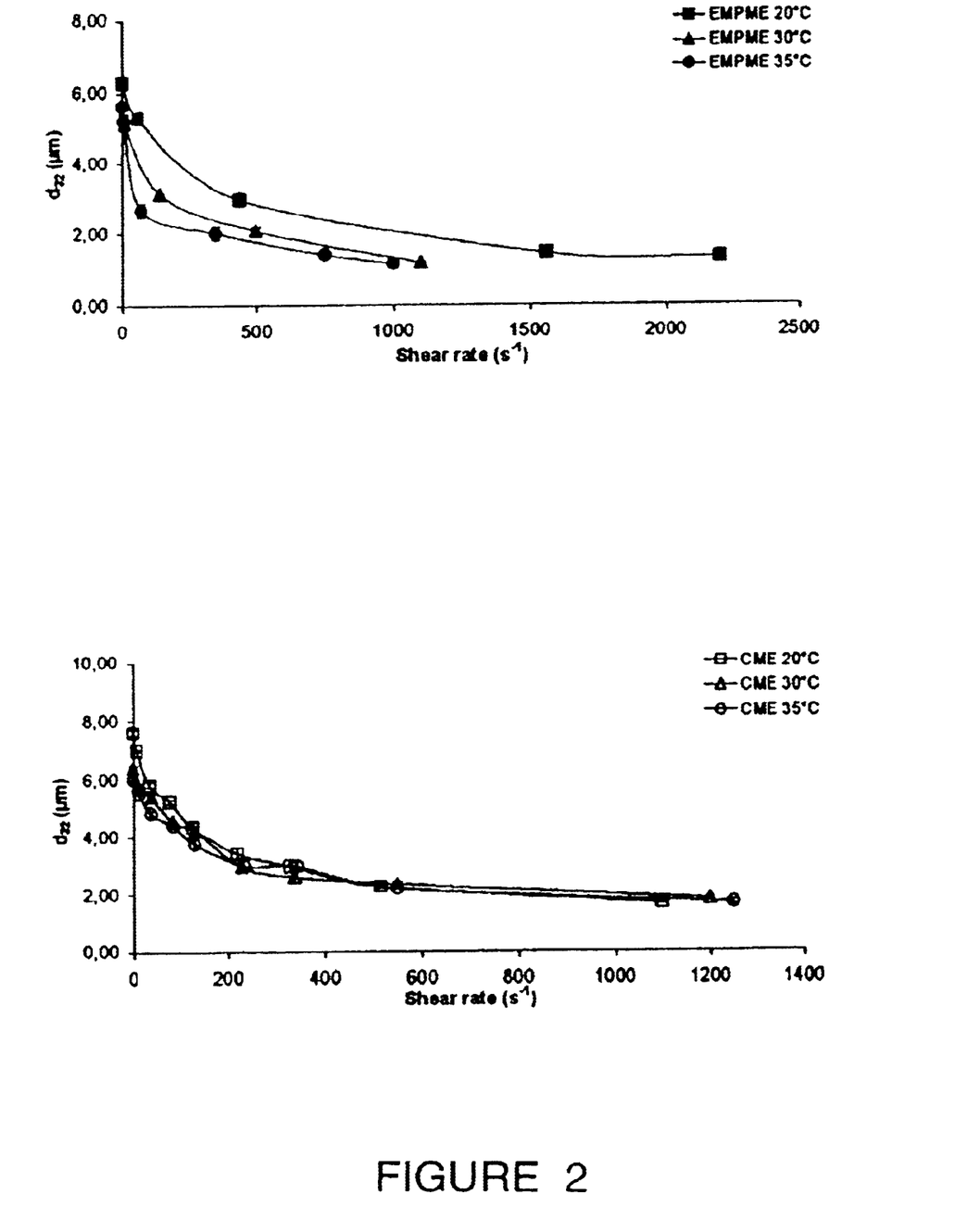
FIG. 2 shows break up curves at different temperatures for (A) EMPME and (B) a Carbopol® (lightly crosslinked poly(acrylic acid)) multiple emulsion (CME) (mean±SD $\mu$m, n=3 analyses performed 3 time on the same emulsion; a different emulsion was used at each temperature.

Temperature-Dependent Behaviour Under Shear of the New Thermo-Sensitive W/O/W Multiple Emulsion EMPME Break Up Studies. The mean droplet diameter of the multiple emulsions as a function of shear rate is shown in FIG. 2. The two emulsions tested were shear-sensitive, as indicated by the decrease of mean diameter with increasing shear. However, whereas no significant temperature effects were observed with CME, which was not so surprising since the carbopol viscosity does not vary with temperature, major temperature effects were noted with EMPME. The decrease of the mean diameter after shearing for 3 min at 100 $s^{-1}$ was only 22% at 20° C. instead of 55% at 35° C. Of course, this could be explained by the viscosity increase of the EMP Hydrogel™ at higher temperatures.

Figure 3:
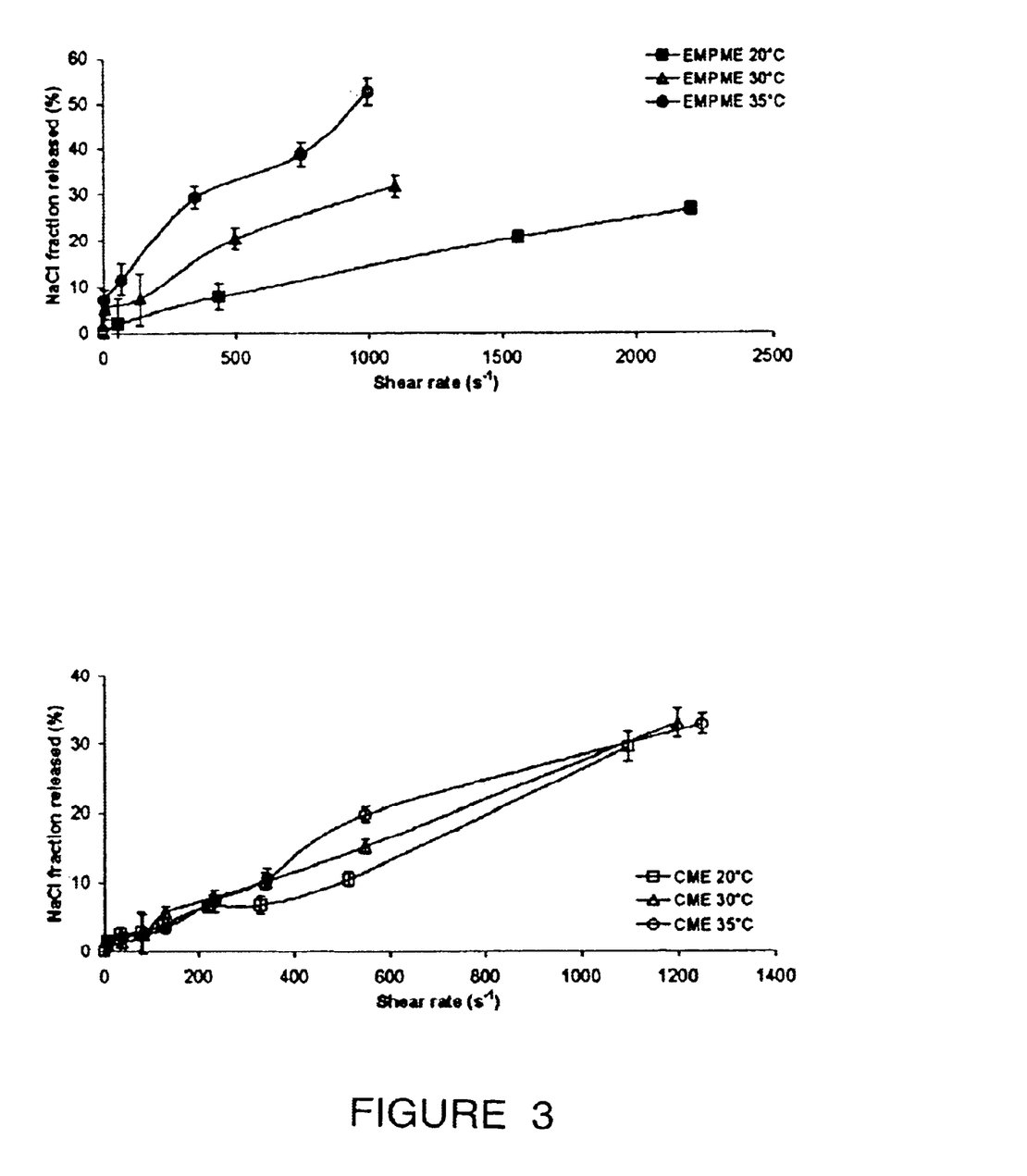
FIG. 3 shows release curves at different temperatures for (A) EMPME and (B) CME (mean±SD %, n=3 analyses performed 3 time on the same emulsion).
Figure 4:
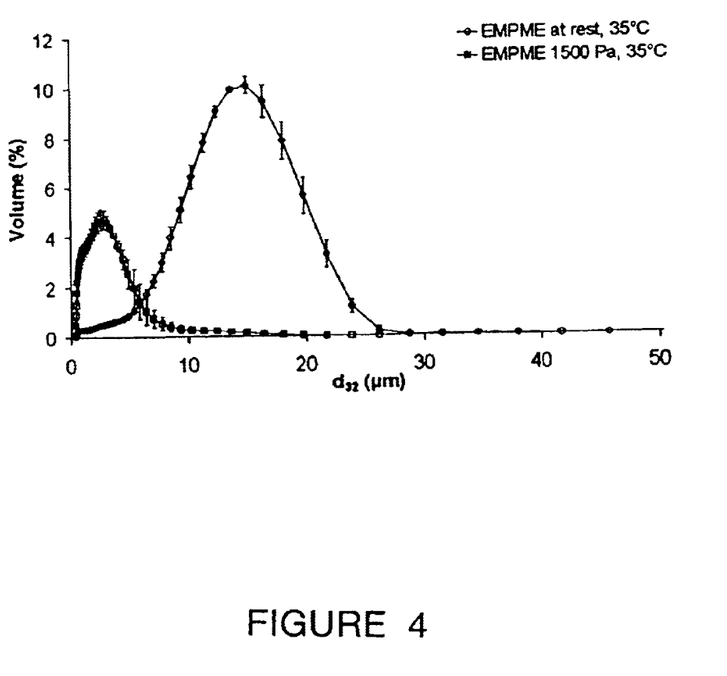
FIG. 4 shows granulometric distributions obtained for EMPME at rest and submitted to a 1500 Pa shear stress (1000 s$^{-1}$), at 35° C. (mean±SD $\mu$m, n=3 analyses performed 3 tim on the same emulsion; a different emulsion was used at each temperature.

Release Studies. The fractional release of NaCl as a function of the shear rate for the two multiple emulsions is presented in FIG. 3. It is noteworthy that the higher release percentages were observed with EMPME at 35° C., even for the low shear rates. Contrary to the results obtained with CME, the fraction released from EMPME were temperature-dependent throughout the shear rate range studied. For example, shearing for 3 minutes at 1000 $s^{-1}$ (which is a shear rate usually reached during topic applications) resulted in fractions released of 14% at 20° C., 30% at 30° C. and 53% at 35° C. Also, it may be observed that, at 35° C., 25% NaCl is released after shearing of EMPME and CME at 250 $s^{-1}$ and 850 $s^{-1}$, respectively. It is also of interest to note that the release was partial: only half of the total amount of NaCl encapsulated was released. However, as shown in FIG. 4, a single shearing of 3 minutes at 1000 $s^{-1}$ at 35° C. led to at least one fragmentation of each globule.

The entrapment yields were respectively 99.9±0.1% (n=3) and 90±4% (n=3) for EMPME and CME.

INFLUENCE OF THE LIPOPHILIC SURFACANT ON THE RELEASE MECHANISMS

Figure 5:
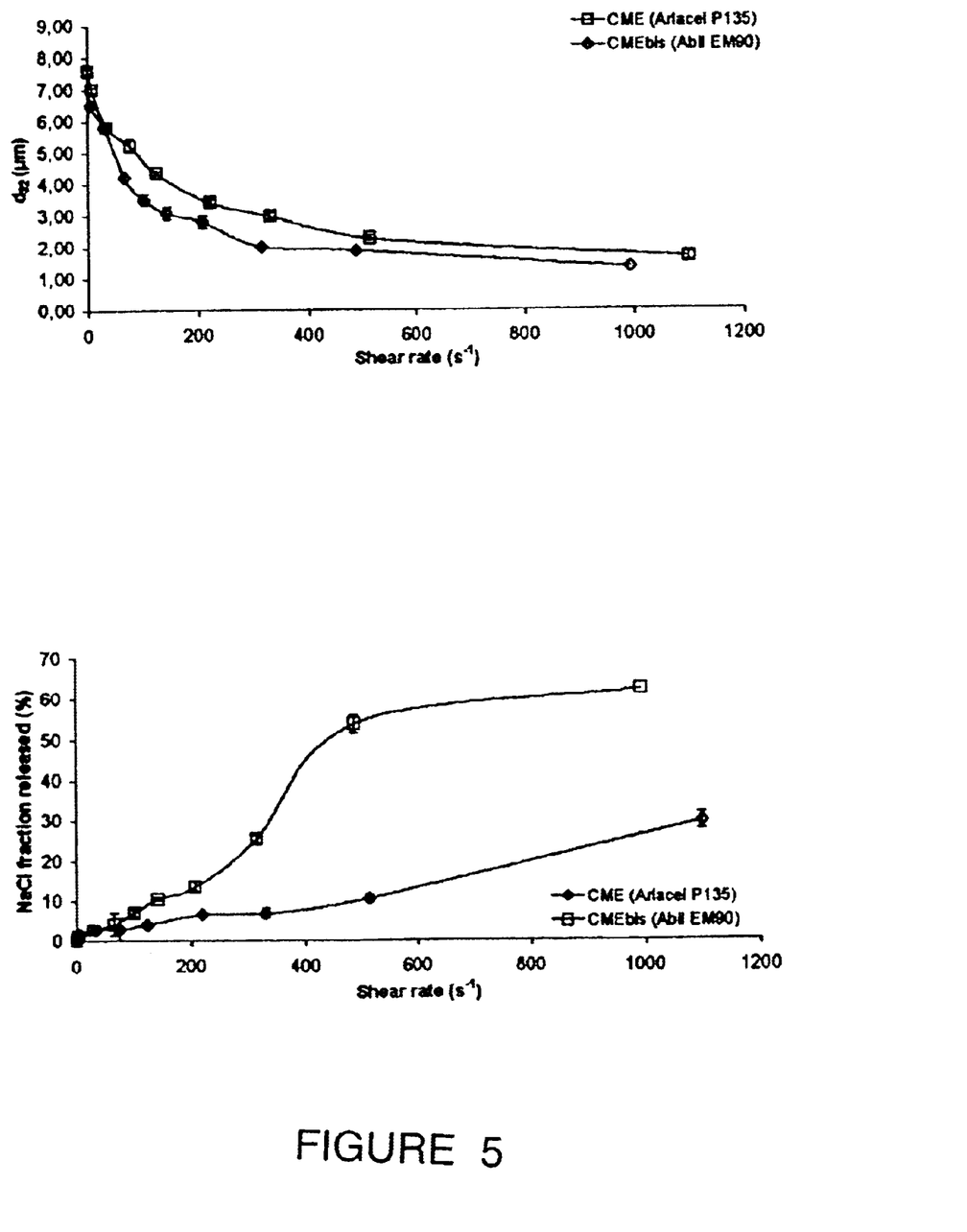
FIG. 5 shows (A) break up and (B) NaCl release curves obtained at 20 to 40° C. with CME formulated with two different lipophilic surfactants, Arlacel® P135 and Abil® EM90 (mean±SD $\mu$m or %, n=3 analyses performed 3 time on the same emulsion; a different emulsion was used at each temperature.

FIG. 5 compares the break up and release curves of CME formulated with Arlacel® P135 and Abil® EM90. Both the fragmentation and the fraction released were higher for the one formulated with Abil® EM90. For example, a 3 minutes shearing at 100 $s^{-1}$ led to a mean diameter decrease of 54% (CMEbis) instead of 22% (CME). The fraction released was largely increased: a 3 minutes shearing at 1000 $s^{-1}$ was 26% for CME formulated with Arlacel® P135 versus 62% for the one formulated with Abil® EM90.

Multiple emulsion that is insensitive to shear during the fabrication but releases its content upon application under conditions modelling these in cosmetic formulations (i.e. upon rubbing against the skin) has been successfully achieved by the design of a new heat sensitive thermogelling W/O/W emulsion. The specific HMP applied herein consists of poly(acrylic acid) and Pluronic® and appears to be an effective thickener, both in aqueous solutions and in multiple emulsions.

As shown by the break up and release data, the fraction released of NaCl increased with the temperature. In comparison with a more classical multiple emulsion thickened by the temperature-insensitive Carbopol® 974-P, the EMPME presented some interesting advantages. Firstly, this W/O/W multiple emulsion may be prepared by an easy two step process (instead of three steps for CME). Secondly, the reproducibility of the EMPME emulsion may be better: the third fabrication stage of CME, consisting in neutralization by NaOH, mixing with a flexible spatula, was a step not easily controllable. Thirdly, the mean encapsulation yield with EMPME was higher than with CME (99.9±0.1% against 90±4%), due to the low viscosity of EMP Hydrogel™ around 15° C. (temperature of fabrication) making this emulsion practically insensitive to shear at this moment. Lastly, the release under a shear comparable to skin application of EMPME (around 33–35° C.) would be higher than the CME one, although it was not as dramatic as the granulometric distribution showed in FIG. 4 foresaw. If the coalescence phenomenon, which is generally not observed in the literature for multiple emulsions, may be excluded, two mechanisms could explain this partial release from the W/O/W emulsions. The first one could be a healing phenomenon, i.e. immediate reformation of two smaller droplets after break up of the initial globule under shear. An excess of surfactant could induce it. The second one, already described by Srinivasan and Stroeve could result from the fact that sheared microdroplets are covered by a thin film of oily phase, preventing in this way the electrolyte release. With regard to the first hypothesis, we have noted that the use of Abil® EM90 instead of Arlacel® P135 in W/O/W multiple emulsion led to a higher fraction released (62% released instead of 26%, after a 3 minutes shearing at 100 $s^{-1}$ at 20° C.). As Abil® EM90 is of higher molecular weight (15000 instead of 5000 for Arlacel® P135), we think that this one was slower to move and thus diminished the healing phenomenon. The use of this lipophilic surfactant in further formulations would be very beneficial to reduce the partial release.

The ease of fabrication of the EMP-modified multiple emulsions and superior release characteristics of the modified emulsions (EMPME) suggest numerous applications in the controlled release of drugs. In particular, it finds use in topical pharmaceutical and cosmetic applications. The emulsion is stable at room temperature and of low viscosity, so that the emulsion stable during fabrication, packing and storage. However, at body (skin) temperatures, the emulsion thickens dramatically. The viscosity can increase many fold, e.g., 5-fol, 10-fold, 100-fold or higher. The increase viscosity increase shear upon topical application, which encourages rupture of the droplets and release of the active agent. The use of multiple emulsions provides both hydrophilic and lipophilic encapsulation domains for sequestering both hydrophilic and hydrophobic active agents.

What is claimed is:

1. A thermally reversible water in oil in water (W/O/W) emulsion having a continuous aqueous phase comprising a thermally reversible viscosifying polymer, the thermally reversible polymer comprising 0.01 to 20 wt % of the continuous aqueous phase, wherein the viscosity of the emulsion increases about 2-fold to about 100-fold in response to an increase in temperature.

2. A thermally reversible water in oil in water (W/O/W) emulsion having a continuous aqueous phase comprising a thermally reversible viscosifying polymer, wherein the thermally reversible viscosifying polymer comprises a block copolymer comprising at least a first polyoxyalkylene block having a hydrophobic region and a hydrophilic region effective to form micelles in solution in response to a change in temperature, and at least a second block comprising a poly(vinylcarboxylic acid).

3. The W/O/W emulsion of claim 2, wherein the block copolymer is a linear block copolymer.

4. The W/O/W emulsion of claim 2, wherein the block copolymer is a random block copolymer.

5. The composition of claim 2, wherein said polyoxyalkylene comprises polyoxyethylene as the hydrophilic region and polyoxypropylene as the hydrophobic region.

6. The composition of claim 2, wherein the poly(vinylcarboxylic acid) is selected from the group consisting of acrylic acid, substituted acrylic acids, methacrylic acid, substituted methacrylic acids, and ionized forms thereof.

7. The composition of claim 2, wherein the polyoxyalkylene comprises a triblock polymer of polyoxyethylene (POE) and polyoxypropylene (POP) having the formula $(POE)_a(POP)_b(POE)_a$, where a is in the range of 100–50, and b is in the range of 50–70.

8. The composition of claim 1, wherein the viscosity increase occurs at a temperature in the range of about 20 to 40° C.

9. The composition of claim 2, wherein the thermally reversible viscosifying polymer comprises about 0.01 to 20 wt % of the continuous aqueous phase.

10. The composition of claim 2, wherein the thermally reversible viscosifying polymer comprises about 0.1 to 10 wt % of the continuous aqueous phase.

11. The composition of claim 2, wherein the thermally reversible viscosifying polymer comprises about 0.01 to 1 wt % of the continuous aqueous phase.

12. The emulsion of claim 1, wherein active agents are entrapped within a discontinuous water phase of the W/O/W emulsion.

13. The emulsion of claim 1, wherein active agents are entrapped within oil phase droplets of the W/O/W emulsion.

14. A pharmaceutical composition, comprising:
   a water in oil in water emulsion having a continuous aqueous phase, wherein the continuous aqueous phase comprises a thermally reversible viscosifying polymer, the thermally reversible viscosifying polymer comprising 0.01 to 20 wt % of the continuous aqueous phase, wherein the viscosity of the emulsion increases about 2-fold to about 100-fold in response to an increase in temperature; and
   at least one active agent in the oil or water discontinuous phase.

15. The pharmaceutical composition of claim 14, wherein the thermally reversible viscosifying polymer comprises a block copolymer comprising at least a first polyoxyalkylene block having a hydrophobic region and a hydrophilic region effective to form micelles in solution in response to a change in temperature, and at least a second block comprising a poly(vinylcarboxylic acid).

16. The pharmaceutical composition of claim 14, wherein said polyoxyalkylene comprises polyoxyethylene as the hydrophilic region and polyoxypropylene as the hydrophobic region.

17. The pharmaceutical composition of claim 16, wherein the poly(vinylcarboxylic acid) is selected from the group consisting of acrylic acid, substituted acrylic acids, methacrylic acid, substituted methacrylic acids, and ionized forms thereof.

18. The pharmaceutical composition of claim 14, wherein the polyoxyalkylene comprises a triblock polymer of polyoxyethylene (POE) and polyoxypropylene (POP) having the formula $(POE)_a(POP)_b(POE)_a$, where a is in the range of 100–50, and b is in the range of 50–70.

19. The pharmaceutical composition of claim 14, wherein the viscosity increase occurs at a temperature in the range of about 20 to 40° C.

20. The pharmaceutical composition of claim 14, wherein the thermally reversible viscosifying polymer comprises about 0.01 to 10 wt % of the continuous aqueous phase.

21. The pharmaceutical composition of claim 14, wherein the thermally reversible viscosifying polymer comprises about 0.01 to 1 wt % of the continuous aqueous phase.

22. The pharmaceutical composition of claim 14, wherein active agents are entrapped within the discontinuous water phase of the W/O/W emulsion.

23. The pharmaceutical composition of claim 14, wherein active agents are entrapped within oil phase droplets of the W/O/W emulsion.

24. The composition of claim 2, wherein the viscosity of the emulsion increases at a temperature in the range of about 20 to 40° C.

25. The composition of claim 1, wherein the thermally reversible viscosifying polymer comprises about 0.1 to 10 wt % of the continuous aqueous phase.

26. The composition of claim 1, wherein the thermally reversible viscosifying polymer comprises about 0.01 to 1 wt % of the continuous aqueous phase.

27. The emulsion of claim 2, wherein active agents are entrapped within the discontinuous water phase of the W/O/W emulsion.

28. The emulsion of claim 2, wherein active agents are entrapped within oil phase droplets of the W/O/W emulsion.

* * * * *